United States Patent [19]

Wilson et al.

[11] Patent Number: 6,165,668

[45] Date of Patent: Dec. 26, 2000

[54] N-[2-(1,2-BENZISOTHIAZOL-3(2H)-YLIDENE 1,1-DIOXIDE)-2-CYANOACETYL] BENZENESULFONAMIDE CHARGE CONTROL AGENTS FOR ELECTROSTATOGRAPHIC TONERS AND DEVELOPERS

[75] Inventors: John C. Wilson; Robert D. Fields, both of Rochester, N.Y.

[73] Assignee: Eastman Kodak Company, Rochester, N.Y.

[21] Appl. No.: 09/464,203

[22] Filed: Dec. 15, 1999

[51] Int. Cl.⁷ .......................... G03G 9/097; C07D 275/04
[52] U.S. Cl. ............................. 430/110; 548/207
[58] Field of Search ................... 430/110, 109; 548/207

[56] References Cited

U.S. PATENT DOCUMENTS

| | | |
|---|---|---|
| 5,405,727 | 4/1995 | Wilson et al. . |
| 5,714,295 | 2/1998 | Wilson et al. . |
| 5,716,749 | 2/1998 | Wilson et al. . |
| 5,719,000 | 2/1998 | Wilson et al. . |
| 5,719,001 | 2/1998 | Wilson et al. . |
| 5,723,249 | 3/1998 | Wilson et al. . |
| 5,739,235 | 4/1998 | Wilson et al. . |
| 5,744,277 | 4/1998 | Wilson et al. . |
| 5,750,715 | 5/1998 | Wilson et al. . |
| 5,766,815 | 6/1998 | Wilson et al. . |
| 5,821,024 | 10/1998 | Wilson et al. . |
| 5,821,025 | 10/1998 | Wilson et al. . |
| 5,922,499 | 7/1999 | Wilson et al. . |
| 5,976,753 | 11/1999 | Wilson et al. . |

*Primary Examiner*—Christopher D. Rodee
*Attorney, Agent, or Firm*—Christ P. Konkol

[57] ABSTRACT

An electrophotographic toner is disclosed comprising a polymeric binder and an N-[2-(1,2-benzisothiazol-3(2H)-ylidene 1,1 -dioxide)-2-cyanoacetyl]benzenesulfonamide as charge control agent having the structure:

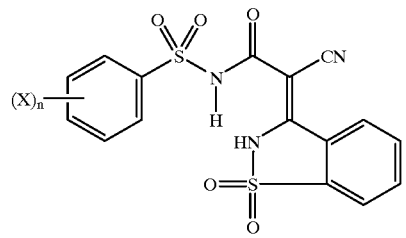

wherein n and X are defined in the specification. The compounds are useful as charge control agents in electrostatographic toners and developers.

8 Claims, No Drawings

N-[2-(1,2-BENZISOTHIAZOL-3(2H)-YLIDENE 1,1-DIOXIDE)-2-CYANOACETYL] BENZENESULFONAMIDE CHARGE CONTROL AGENTS FOR ELECTROSTATOGRAPHIC TONERS AND DEVELOPERS

FIELD OF THE INVENTION

The present invention relates to electrostatographic developers and toners containing charge control agents.

BACKGROUND OF THE INVENTION

In electrography, image charge patterns are formed on a support and are developed by treatment with an electrographic developer containing marking particles which are attracted to the charge patterns. These particles are called toner particles or, collectively, toner. Two major types of developers, dry and liquid, are employed in the development of the charge patterns.

In electrostatography, the image charge pattern, also referred to as an electrostatic latent image, is formed on an insulative surface of an electrostatographic element by any of a variety of methods. For example, the electrostatic latent image may be formed electrophotographically, by image-wise photo-induced dissipation of the strength of portions of an electrostatic field of uniform strength previously formed on the surface of an electrophotographic element comprising a photoconductive layer and an electrically conductive substrate. Alternatively, the electrostatic latent image may be formed by direct electrical formation of an electrostatic field pattern on a surface of a dielectric material.

One well-known type of electrostatographic developer comprises a dry mixture of toner particles and carrier particles. Developers of this type are employed in cascade and magnetic brush electrostatographic development processes. The toner particles and carrier particles differ triboelectrically, such that during mixing to form the developer, the toner particles acquire a charge of one polarity and the carrier particles acquire a charge of the opposite polarity. The opposite charges cause the toner particles to cling to the carrier particles. During development, the electrostatic forces of the latent image, sometimes in combination with an additional applied field, attract the toner particles. The toner particles are pulled away from the carrier particles and become electrostatically attached, in image-wise relation, to the latent image bearing surface. The resultant toner image can then be fixed, by application of heat or other known methods, depending upon the nature of the toner image and the surface, or can be transferred to another surface and then fixed.

Toner particles often include charge control agents which desirably provide uniform net electrical charge to toner particles without reducing the adhesion of the toner to paper or other medium. Many types of positive charge control agents, materials which impart a positive charge to toner particles in a developer, have been used and are described in the published patent literature. In contrast, relatively few negative charge control agents, materials which impart a negative charge to toner particles in a developer, are known.

Prior negative charge control agents have a variety of shortcomings. Many charge control agents are dark colored and cannot be readily used with pigmented toners, such as cyan, magenta, yellow, red, blue, and green. Some are highly toxic or produce highly toxic by-products. Some are highly sensitive to environmental conditions such as humidity. Some exhibit high throw-off or adverse triboelectric properties in some uses. Use of charge control agents requires a balancing of shortcomings and desired characteristics to meet a particular situation.

The prior art discloses the use of 1,2-benzisothiazol-3 (2H)-ylidene 1,1-dioxides as negative charge control agents for electrophotographic toners and developers. The general structural formula for this class of compounds is represented as:

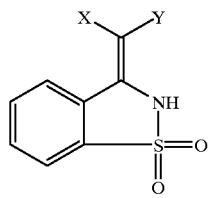

This prior art includes U.S. Pat. Nos. 5,744.277, 5,719,001, 5,976,753, 5,821,025, 5,766,815, 5,714,295, 5,716,749, 5,750,715, 5,719,000, 5,723,249, 5,821,024, 5,922,499, 5,739,235 and 5,405,727. Of particular relevance, U.S. Pat. No. 5,766,815 discloses compositions with the general structural formula:

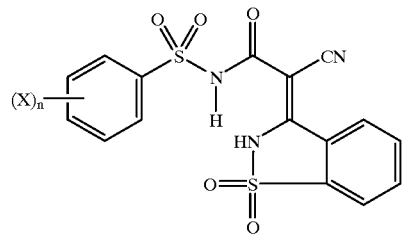

It would be highly desirable to obtain negative charge control agents useful in electrostatographic toners and developers which agents have favorable charging and other relevant characteristics.

SUMMARY OF THE INVENTION

The invention provides an electrophotographic toner comprising a polymeric binder and an N-[2-(1,2-benzisothiazol-3(2H)-ylidene 1,1-dioxide)-2-cyanoacetyl] benzenesulfonamide as charge control agent having the structure:

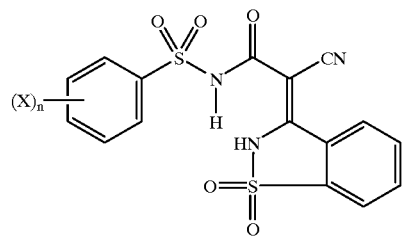

wherein
  n represents an integer of 1 to 5 and
  X represents hydrogen, alkyl, alkoxy, halo, nitro, amino, hydroxyl, carboalkoxy, carboxy, keto, formyl, alkyl sulfonate, sulfonamido or sulfamyl.

The charge control agents are useful in electrostatographic toners and developers. It is an advantageous effect of the invention that negatively charging toners can be provided which have favorable charging characteristics.

DETAILED DESCRIPTION OF THE INVENTION

The term "particle size" as used herein, or the term "size," or "sized" as employed herein in reference to the term "particles," means the median volume weighted diameter as measured by conventional diameter measuring devices, such as a Coulter Multisizer, sold by Coulter, Inc. of Hialeah, Fla. Median volume weighted diameter is an equivalent weight spherical particle which represents the median for a sample; that is, half of the mass of the sample is composed of smaller particles, and half of the mass of the sample is composed of larger particles than the median volume weighted diameter.

The term "charge control," as used herein, refers to a propensity of a toner addendum to modify the triboelectric charging properties of the resulting toner.

The term "glass transition temperature" or "$T_g$," as used herein, means the temperature at which a polymer changes from a glassy state to a rubbery state. This temperature ($T_g$) can be measured by differential thermal analysis as disclosed in "Techniques and Methods of Polymer Evaluation," Vol. 1, Marcel Dekker, Inc., New York, 1966.

As indicated above, the invention provides an electrophotographic toner having polymeric binder and, as charge control agents, compounds referred to as N-[2-(1,2-benzisothiazol-3(2H)-ylidene 1,1 -dioxide)-2-cyanoacetyl]benzenesulfonamides, having the following structure:

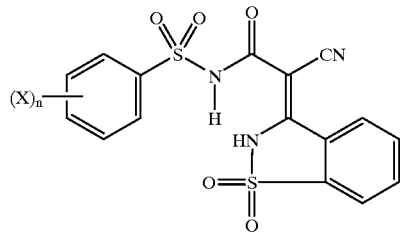

where n represents an integer of 1 to 5 and X represents hydrogen, alkyl, alkoxy, halo, nitro, amino, hydroxyl, carboalkoxy, carboxy, keto, formyl, alkylsulfonate, sulfonamido, sulfamyl, etc. By halo is meant bromo, chloro, iodo, and/or fluoro groups. The alkyl and alkoxy groups suitably include those containing 1 to 12 carbons, preferably 1 to 6 carbons, most preferably 1 to 3 carbon atoms.

A preferred group of compounds have the following structure:

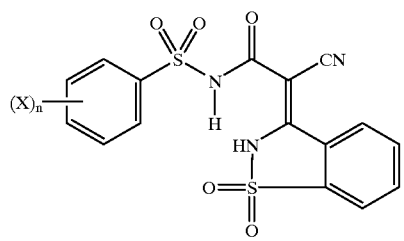

where n is 1 and X represents methyl, nitro, or chloro.

Exemplary N-[2-( 1,2-benzisothiazol-3(2H)-ylidene 1,1-dioxide)-2-cyanoacetyl]benzenesulfonamides according to the above structure are N-[2-(1,2-benzisothiazol-3(2H)-ylidene 1,1-dioxide)-2-cyanoacetyl]benzenesulfonamide, N-[2-(1,2-benzisothiazol-3(2H)-ylidene 1,1-dioxide)-2-cyanoacetyl]-4-methylbenzenesulfonamide, N-[2-(1,2-benzisothiazol-3(2H)-ylidene 1,1 -dioxide)-2-cyanoacetyl]-4-methoxybenzenesulfonamide, N-[2-(1,2-benzisothiazol-3(2H)-ylidene 1,1-dioxide)-2-cyanoacetyl]-4-chlorobenzenesulfonamide, N-[2-(1,2-benzisothiazol-3(2H)-ylidene 1,1-dioxide)-2-cyanoacetyl]-4-nitrobenzenesulfonamide, N-[2-( 1,2-benzisothiazol-3(2H)-ylidene 1,1-dioxide)-2-cyanoacetyl]-4-aminobenzenesulfonamide, N-[2-(1,2-benzisothiazol-3(2H)-ylidene 1,1-dioxide)-2-cyanoacetyl]-4-hydroxybenzenesulfonamide, N-[2-(1,2-benzisothiazol-3(2H)-ylidene 1,1-dioxide)-2-cyanoacetyl]-4-carbomethoxybenzenesulfonamide, N-[2-(1,2-benzisothiazol-3(2H)-ylidene 1,1-dioxide)-2-cyanoacetyl]-4-acetylbenzenesulfonamide, N-[2-(1,2-benzisothiazol-3(2H)-ylidene 1,1-dioxide)-2-cyanoacetyl]-4-formylbenzenesulfonamide, N-[2-(1,2-benzisothiazol-3(2H)-ylidene 1,1-dioxide)-2-cyanoacetyl]-4-methoxysulfonylbenzenesulfonamide, N-[2-(1,2-benzisothiazol-3 (2H)-ylidene 1,1-dioxide)-2-cyanoacetyl]-4-sulfonamidobenzenesulfonamide, N-[2-(1,2-benzisothiazol- 3(2H)-ylidene 1,1-dioxide)-2-cyanoacetyl]-4-sulfamylbenzenesulfonamide, N-[2-(1,2-benzisothiazol-3(2H)-ylidene 1,1-dioxide)-2-cyanoacetyl]-3,5-di(t-butyl)-4-hydroxybenzenesulfonamide, N-[2-(1,2-benzisothiazol-3(2H)-ylidene 1,1-dioxide)-2-cyanoacetyl]-2,4,6-trimethylbenzenesulfonamide, N-[2-(1,2-benzisothiazol-3(2H)-ylidene 1,1-dioxide)-2-cyanoacetyl]-3-chlorobenzenesulfonamide, N-[2-(1,2-benzisothiazol-3(2H)-ylidene 1,1-dioxide)-2-cyanoacetyl]-2,3,5,6-tetramethylbenzenesulfonamide, and N-[2-(1,2-benzisothiazol-3(2H)-ylidene 1,1-dioxide)-2-cyanoacetyl]-2,3,4,5,6-pentamethylbenzenesulfonamide.

N-[2-(1,2-Benzisothiazol-3(2H)-ylidene 1,1-dioxide)-2-cyanoacetyl]benzenesulfonamides may be prepared by condensing 3-chloro- 1,2-benzisothiazole 1,1-dioxide (prepared as described in J. Chem. Soc., 1957, 490), with N-(cyanoacetyl)benzenesulfonamides with triethylamine as acid acceptor.

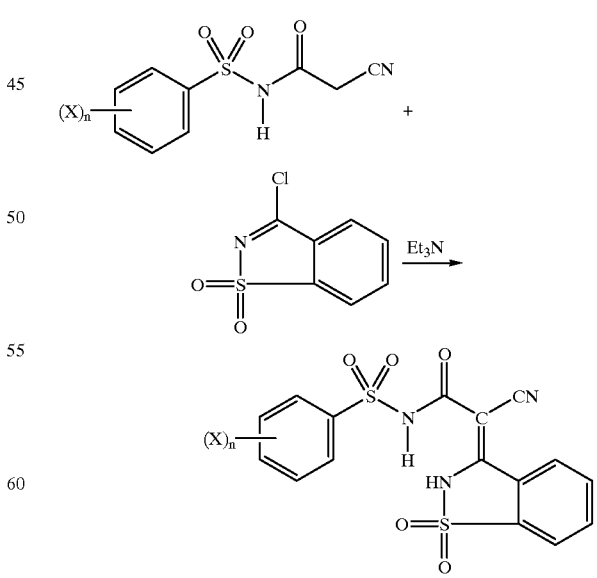

The compounds of the invention can generally tautomerize. Thus, the structure would also include the tautomeric forms:

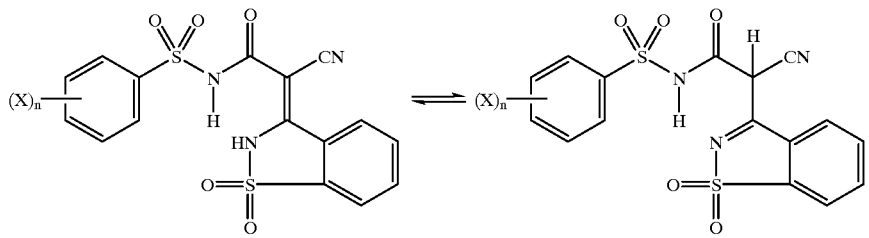

For the sake of brevity, alternate tautomeric forms will not be illustrated herein. However, formulas should be understood to be inclusive of alternate tautomers. In addition to tautomeric forms, the compositions of the invention may, with respect to the 3-ylidene double bond, exist as geometric isomers.

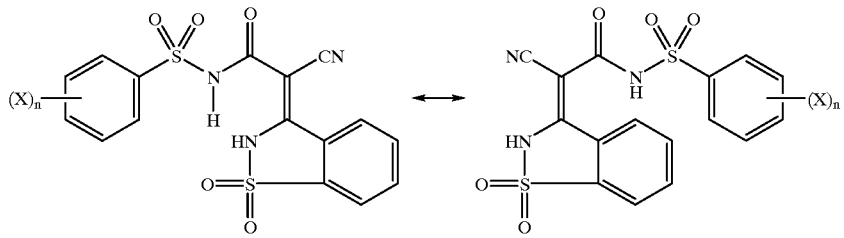

Although the configuration of the compounds of the invention is unknown, both geometric isomers are considered to fall within the scope of the invention.

The toners of the invention include a charge control agent of the invention, in an amount effective to modify, and improve the properties of the toner. It is preferred that a charge control agent improve the charging characteristics of a toner, so the toner quickly charges to a negative value having a suitable absolute magnitude and then maintains about the same level of charge. The compositions used in the toners are negative charge control agents, thus the toners of the invention achieve and maintain negative charges.

It is also preferred that a charge control agent improve the charge uniformity of a toner composition, that is, it insures that substantially all of the individual toner particles exhibit a triboelectric charge of the same sign with respect to a given carrier. The charge control agents of the invention are generally lightly colored. The charge control agents of the invention are metal free and have good thermal stability. Preferred materials described herein are based upon an evaluation in terms of a combination of characteristics rather than any single characteristic.

The binders used in formulating the toners of the invention with the charge controlling additive of the present invention are polyesters having a glass transition temperature of 40 to 120° C., preferably 50° to 100° C. and a weight average molecular weight of 2,000 to 150,000, preferably 10,000 to 100,000. The polyesters are prepared from the reaction product of a wide variety of diols and dicarboxylic acids. Some specific examples of suitable diols are: 1,4-cyclohexanediol; 1,4-cyclohexanedimethanol; 1,4-cyclohexanediethanol; 1,4-bis(2 -hydroxyethoxy) cyclohexane; 1,4-benzenedimethanol; 1,4-benzenediethanol; norbomylene glycol; decahydro-2,6-naphthalenedimethanol; bisphenol A; ethylene glycol; diethylene glycol; triethylene glycol; 1,2-propanediol, 1,3-propanediol; 1,4-butanediol; 2,3-butanediol; 1,5-pentanediol; neopentyl glycol; 1,6-hexanediol; 1,7-heptanediol; 1,8-octanediol; 1,9-nonanediol; 1,10-decanediol; 1,12-dodecanediol; 2,2,4-trimethyl-1,6-hexanediol; 4-oxa-2,6-heptanediol and etherified diphenols.

Suitable dicarboxylic acids include: succinic acid; sebacic acid; 2-methyladipic acid; diglycolic acid; thiodiglycolic acid; fumaric acid; adipic acid; glutaric acid; cyclohexane-1,3-dicarboxylic acid; cyclohexane-1,4-dicarboxylic acid; cyclopentane-1,3-dicarboxylic acid; 2,5--norbornanedicarboxylic acid; phthalic acid; isophthalic acid; terephthalic acid; 5-butylisophthalic acid; 2,6-naphthalenedicarboxylic acid; 1,4-naphthalenedicarboxylic acid; 1,5-naphthalenedicarboxylic acid; 4,4'-sulfonyldibenzoic acid; 4,4'-oxydibenzoic acid; binaphthyl-dicarboxylic acid; and lower alkyl esters of the acids mentioned.

Polyfunctional compounds having three or more carboxyl groups, and three or more hydroxyl groups are desirably employed to create branching in the polyester chain. Triols, tetraols, tricarboxylic acids, and functional equivalents, such as pentaerythritol, 1,3,5-trihydroxypentane, 1,5-dihydroxy-3-ethyl-3-(2-hydroxyethyl)pentane, trimethylolpropane, trimellitic anhydride, pyromellitic dianhydride, and the like are suitable branching agents. Presently preferred polyols are glycerol and trimethylolpropane. Preferably, up to about 15 mole percent, preferably 5 mole percent, of the reactant diol/polyol or diacid/polyacid monomers for producing the polyesters can be comprised of at least one polyol having a functionality greater than two or poly-acid having a functionality greater than two.

Variations in the relative amounts of each of the respective monomer reactants are possible for optimizing the physical properties of the polymer.

The polyesters of this invention are conveniently prepared by any of the known polycondensation techniques, e.g., solution polycondensation or catalyzed melt-phase polycondensation, for example, by the transesterification of dimethyl terephthalate, dimethyl glutarate, 1,2-propanediol and glycerol.

The polyesters also can be prepared by two-stage poly-esterification procedures, such as those described in U.S.

Pat. No. 4,140,644 and U.S. Pat. No. 4,217,400. The latter patent is particularly relevant, because it is directed to the control of branching in polyesterification. In such processes, the reactant glycols and dicarboxylic acids, are heated with a polyfunctional compound, such as a triol or tricarboxylic acid, and an esterification catalyst in an inert atmosphere at temperatures of 190 to 280° C., especially 200 to 240° C. Subsequently, a vacuum is applied, while the reaction mixture temperature is maintained at 220 to 240° C., to increase the product's molecular weight.

The degree of polyesterification can be monitored by measuring the inherent viscosity (I.V.) of samples periodically taken from the reaction mixture. The reaction conditions used to prepare the polyesters should be selected to achieve an I.V. of 0.10 to 0.80 measured in methylene chloride solution at a concentration of 0.25 grams of polymer per 100 milliliters of solution at 25° C. An I.V. of 0.10 to 0.60 is particularly desirable to insure that the polyester has a weight average molecular weight of 10,000 to 100,000, preferably 55,000 to 65,000, a branched structure and a Tg in the range of about 50° to about 100° C. Amorphous polyesters are particularly well suited for use in the present invention. After reaching the desired inherent viscosity, the polyester is isolated and cooled.

One useful class of polyesters comprises residues derived from the polyesterification of a polymerizable monomer composiiton comprising:

a dicarboxylic acid-derived component comprising:
about 75 to 100 mole % of dimethyl terephthalate and
about 0 to 25 mole % of dimethyl glutarate and
a diol/poly-derived component comprising
about 90 to 100 mole % of 1,2-propanediol and
about 0 to 10 mole % of glycerol.

Many of the aforedescribed polyesters are disclosed in the patent to Alexandrovich et al, U.S. Pat. No. 5,156,937.

Another useful class of polyesters is the non-linear reaction product of a dicarboxylic acid and a polyol blend of etherified diphenols disclosed in U.S. Pat. Nos. 3,681,106; 3,709,684; and 3,787,526.

A preferred group of etherified bisphenols within the class characterized by the above formula in U.S. Pat. No. 3,787,526 are polyoxypropylene 2,2'-bis(4-hydroxyphenyl) propane and polyoxyethylene or polyoxypropylene, 2,2-bis(4-hydroxy, 2,6-dichlorophenyl) propane wherein the number of oxyalkylene units per mol of bisphenol is from 2.1 to 2.5.

The etherified diphenols disclosed in U.S. Pat. No. 3,709,684 are those prepared from 2,2-bis(4-hydroxy-phenyl) propane or the corresponding 2,6,2',6'-tetrachloro or tetrafluoro bisphenol alkoxylated with from 2 to 4 mols of propylene or ethylene oxide per mol of bisphenol. The etherified diphenols disclosed in U.S. Pat. No. 3,681,106 have ther formula:

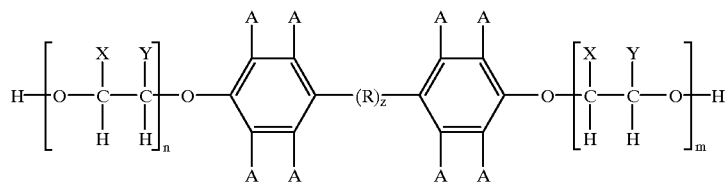

wherein z is 0 or 1, R is an alkylene radical containing from 1 to 5 carbon atoms, a sulfur atom, an oxygen atom,

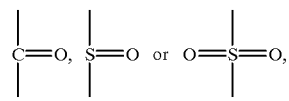

X and Y are individually selected from the group consisting of alkyl radicals containing from 1 to 3 carbon atoms, hydrogen, and a phenyl radical with the limitation that at least X or Y is hydrogen in any X and Y pair on adjacent carbon atoms, n and m are integers with the proviso that the average sum of n and m is from about 2 to about 7; and each A is either a halogen atom or a hydrogen atom. An average sum of n and m means that in any polyol blend some of the etherified diphenols within the above formula may have more than 7 repeating ether units but that the average value for the sum of n and m in any polyhydroxy composition is from 2 to 7. A preferred group of said etherified diphenols are those where the average sum of n and m is from about 2 to about 3. Thus, although the sum of n and m in a given molecule may be as high as about 20, the average sum in the polyol composition will be about 2 to about 3. Examples of these preferred etherified diphenols include:

polyoxyethylene(2.7)-4-hydroxyphenyl-2-chloro-4-hydroxyphenyl ethane;

polyoxyethylene(2.5)-bis(2,6-dibromo-4-hydroxyphenyl) sulfone;

polyoxypropylene(3)-2,2-bis(2,6-difluoro-4-hydroxyphenyl) propane; and polyoxyethylene(1.5)-polyoxypropylene(1.0)-bis(4-hydroxyphenyl) sulfone.

A preferred polyhydroxy composition used in said polyester resins are those polyhydroxy compositions containing up to 2 mol percent of an etherified polyhydroxy compound, which polyhydroxy compound contains from 3 to 12 carbon atoms and from 3 to 8 hydroxyl groups. Exemplary of these polyhydroxy compounds are sugar alcohols, sugar alcohol anhydrides, and mono and disaccharides. A preferred group of said polyhydroxy compounds are soribitol, 1,2,3,6-hexantetrol; 1,4-sorbitan; pentaerythritol, xylitol, sucrose, 1,2,4-butanetriol, 1,2,5-pentanctriol; xylitol; sucrose, 1,2,4-butanetriol; and erythro and threo 1,2,3-butanetriol. Said etherified polyhydroxy compounds are propylene oxide or ethylene oxide derivatives of said polyhydroxy compounds containing up to about 10 molecules of oxide per hydroxyl group of said polyhydroxy compound and preferably at least one molecule of oxide per hydroxyl group. More preferably the molecules of oxide per hydroxyl group is from 1 to 1.5. Oxide mixtures can readily be used. Examples of these derivatives include polyoxyethylene(20) pentaerythritol, polyoxypropylene(6) sorbitol, polyoxyethylene(65) sucrose, and polyoxypropylene(25) 1,4-sorbitan. The polyester resins prepared from this preferred polyhydroxy composition are more abrasion resistant and usually have a lower liquid point than other crosslinked polyesters herein disclosed.

Polyesters that are the non-linear reaction product of a dicarboxylic acid and a polyol blend of etherified polyhydroxy compounds, discussed above, are commercially available from Reichhold Chemical Company or Kao Corp. To illustrate the invention the examples provided herein use an poly(etherified bisphenol A fumarate) sold as Atlac 382ES by Reichhold.

An optional but preferred component of the toners of the invention is colorant: a pigment or dye. Suitable dyes and pigments are disclosed, for example, in U.S. Pat. No. Re. 31,072 and in U.S. Pat. Nos. 4,160,644; 4,416,965; 4,414,152; and 2,229,513. One particularly useful colorant for toners to be used in black and white electrostatographic copying machines and printers is carbon black. Colorants are generally employed in the range of from about 1 to about 30 weight percent on a total toner powder weight basis, and preferably in the range of about 2 to about 15 weight percent.

The toners of the invention can also contain other additives of the type used in previous toners, including leveling agents, surfactants, stabilizers, and the like. The total quantity of such additives can vary. A present preference is to employ not more than about 10 weight percent of such additives on a total toner powder composition weight basis.

The toners can optionally incorporate a small quantity of low surface energy material, as described in U.S. Pat. Nos. 4,517,272 and 4,758,491. Optionally the toner can contain a particulate additive on its surface such as the particulate additive disclosed in U.S. Pat. No. 5,192,637.

A preformed mechanical blend of particulate polymer particles, charge control agent, colorants and additives can, alternatively, be roll milled or extruded at a temperature sufficient to melt blend the polymer or mixture of polymers to achieve a uniformly blended composition. The resulting material, after cooling, can be ground and classified, if desired, to achieve a desired toner powder size and size distribution. For a polymer having a "$T_g$" in the range of about 50° C. to about 120° C., a melt blending temperature in the range of about 90° C. to about 150° C. is suitable using a roll mill or extruder. Melt blending times, that is, the exposure period for melt blending at elevated temperature, are in the range of about 1 to about 60 minutes. After melt blending and cooling, the composition can be stored before being ground. Grinding can be carried out by any convenient procedure. For example, the solid composition can be crushed and then ground using, for example, a fluid energy or jet mill, such as described in U.S. Pat. No. 4,089,472. Classification can be accomplished using one or two steps.

In place of blending, the polymer can be dissolved in a solvent in which the charge control agent and other additives are also dissolved or are dispersed. The resulting solution can be spray dried to produce particulate toner powders. Limited coalescence polymer suspension procedures as disclosed in U.S. Pat. No. 4,833,060 are particularly useful for producing small sized, uniform toner particles.

The toner particles have an average diameter between about 0.1 micrometers and about 100 micrometers, and desirably have an average diameter in the range of from about 1.0 micrometer to 30 micrometers for currently used electrostatographic processes. The size of the toner particles is believed to be relatively unimportant from the standpoint of the present invention; rather the exact size and size distribution is influenced by the end-use application intended. So far as is now known, the toner particles can be used in all known electrostatographic copying processes.

The amount of charge control agent used typically is in the range of about 0.2 to 10.0 parts per hundred parts of the binder polymer. In particularly useful embodiments, the charge control agent is present in the range of about 1.0 to 4.0 parts per hundred.

The developers of the invention include carriers and toners of the invention. Carriers can be conductive, non-conductive, magnetic, or non-magnetic. Carriers are particulate and can be glass beads; crystals of inorganic salts such as ammonium chloride, or sodium nitrate; granules of zirconia, silicon, or silica; particles of hard resin such as poly(methyl methacrylate); and particles of elemental metal or alloy or oxide such as iron, steel, nickel, carborundum, cobalt, oxidized iron and mixtures of such materials. Examples of carriers are disclosed in U.S. Pat. Nos. 3,850,663 and 3,970,571. Especially useful in magnetic brush development procedures are iron particles such as porous iron, particles having oxidized surfaces, steel particles, and other "hard" and "soft" ferromagnetic materials such as gamma ferric oxides or ferrites of barium, strontium, lead, magnesium, copper, zinc or aluminum. Copper-zinc ferrite powder is used as a carrier in the examples hereafter. Such carriers are disclosed in U.S. Pat. Nos. 4,042,518; 4,478,925; and 4,546,060.

Carrier particles can be uncoated or can be coated with a thin layer of a film-forming resin to establish the correct triboelectric relationship and charge level with the toner employed. Examples of suitable resins are the polymers described in U.S. Pat. Nos. 3,547,822; 3,632,512; 3,795,618 and 3,898,170 and Belgian Patent No. 797,132. Polymeric siloxane coatings can aid the developer to meet the electrostatic force requirements mentioned above by shifting the carrier particles to a position in the triboelectric series different from that of the uncoated carrier core material to adjust the degree of triboelectric charging of both the carrier and toner particles. The polymeric siloxane coatings can also reduce the frictional characteristics of the carrier particles in order to improve developer flow properties; reduce the surface hardness of the carrier particles to reduce carrier particle breakage and abrasion on the photoconductor and other components; reduce the tendency of toner particles or other materials to undesirably permanently adhere to carrier particles; and alter electrical resistance of the carrier particles.

In a particular embodiment, the developer of the invention contains from about 1 to about 20 percent by weight of toner of the invention and from about 80 to about 99 percent by weight of carrier particles. Usually, carrier particles are larger than toner particles. Conventional carrier particles have a particle size of from about 5 to about 1200 micrometers and are generally from 20 to 200 micrometers.

Carriers can also be in liquid form. Useful liquifiable carriers are disclosed in U.S. Pat. Nos. 3,520,681; 3,975,195; 4,013,462; 3,707,368; 3,692,516 and 3,756,812. The carrier can comprise an electrically insulating liquid such as decane, paraffin, Sohio Odorless Solvent 3440 (a kerosene fraction marketed by the Standard Oil Company, Ohio), various isoparaffinic hydrocarbon liquids, such as those sold under the trademark Isopar G by Exxon Corporation and having a boiling point in the range of 145° C. to 186° C., various halogenated hydrocarbons such as carbon tetrachloride, trichloromonofluoromethane, and the like, various alkylated aromatic hydrocarbon liquids such as the alkylated benzenes, for example, xylenes, and other alkylated aromatic hydrocarbons such as are described in U.S. Pat. No. 2,899,335. An example of one such useful alkylated aromatic hydrocarbon liquid which is commercially available is Solvesso® 100 sold by Exxon Corporation.

The toners of the invention are not limited to developers which have carrier and toner, and can be used, without carrier, as single component developer.

The toner and developer of the invention can be used in a variety of ways to develop electrostatic charge patterns or latent images. Such developable charge patterns can be prepared by a number of methods and are then carried by a suitable element. The charge pattern can be carried, for example, on a light sensitive photoconductive element or a non-light-sensitive dielectric surface element, such as an insulator coated conductive sheet. One suitable development technique involves cascading developer across the electrostatic charge pattern. Another technique involves applying toner particles from a magnetic brush. This technique involves the use of magnetically attractable carrier cores. After imagewise deposition of the toner particles the image can be fixed, for example, by heating the toner to cause it to fuse to the substrate carrying the toner. If desired, the unfused image can be transferred to a receiver such as a blank sheet of copy paper and then fused to form a permanent image.

The invention is further illustrated by the following Examples. Thermogravimetric analyses were measured with a Perkin-Elmer Series 7 Thermal Analysis system at a heating rate of 10° C./min in air from 25–500° C.

EXAMPLES

Preparation of Charge Control Agents

This Example illustrates the preparation of N-[2-(1,2-benzisothiazol-3(2H)-ylidene 1,1-dioxide)-2-cyanoacetyl]-4-methylbenzenesulfonamide (Compound 1 in Table 1 below). The compound 3-chloro-1,2-benzisothiazole 1,1-dioxide was prepared by the method of Stephen, et al., J. Chem. Soc., 1957, 490. The N-(cyanoacetyl) benzenesulfonamides were prepared by the method described in Ukr. Khim. Zhur., 33(12),1290 (1967). All other chemicals were commercially available. To a solution of 10.08 g (50 mmol) of 3-chloro-1,2-benzisothiazole 1,1-dioxide, 11.91 g (50 mmol) of N-cyanoacetyl-4-methylbenzenesulfonamide and 100 ml of THF was added dropwise 15.18 g (150 mmol) of triethylamine over a period of 15 mins. The reaction mixture became yellow and warm with the formation of solid. The reaction mixture was stirred for another 6 hrs and poured into dilute HCl. The solid was collected, washed with water then with methanol. The solid was washed with hot isopropanol, collected, washed with ether and dried. The yield of product was 7.22g (35.8% of theory); mp=211–12° C.

Analytical data on this compound and two analogously prepared compounds are shown in Table 1 below.

with chilled water. A known weight of the charge control agent (CCA) was then compounded into the melt. An example batch formula would be 25 g of polyester and 0.5 g of CCA, giving a product with 2 part CCA per 100 parts of polymer. The melt was compounded for 15 minutes, peeled from the mill and cooled. The melt was coarse ground in a Thomas-Wiley laboratory mechanical mill using a 2 mm screen. The resulting material was fine ground in a Trost® TX air jet mill at a pressure of 70 psi and a feed rate of 1 g/hr. The ground toner has a mean volume average particle size of approximately 8.5 microns.

Following the above procedure, clear toners containing only charge control agent and polyester were made for each CCA. Employing the same compounding and grinding procedure a control toner containing no charge agent was also prepared. Developers based on these toners were subsequently prepared to determine the effect of the CCA on toner charging properties.

Preparation of Developers

Developers comprising a mixture of toner and carrier particles was prepared for each charge agent evaluated. Two different types of carrier particles were used in the study. The first type was a copper zinc ferrite (Carrier Type A) coated with a proprietary coating. The second type was a strontium ferrite (Carrier Type B) coated with polysiloxane and has been described in U.S. Pat. No. 4,478,925. Both coated carriers were obtained from PowderTech Corp. (Indiana). Developers using this carrier type were formulated at 8% toner concentration: 0.32 g of toner was added to 3.68 g carrier to make a developer.

Testing of Developers

Toner charge was measured by vigorously exercising the developer mix to generate a triboelectrical charge, sampling the developer mix, and then measuring the toner charge with the charge-measurement device.

Two 4 g developers at 8% toner concentration were prepared by weighing 0.32 g toner and 3.68 g carrier into two separate 4 dram PE plastic vial (Vial#1 and Vial#2). The developer was mixed together with a spatula. Both capped vials were placed in a Wrist-Shaker. The developer was vigorously shaken at about 2 Hertz and overall amplitude of about 11 cm for 2 minutes to triboelectrically charge the developer

TABLE 1

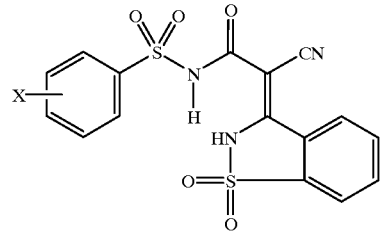

| | | | | | Calcd | | | | | Found | | | | |
|---|---|---|---|---|---|---|---|---|---|---|---|---|---|---|
| EXAMPLE | X | Yield, % | mp, ° C. | TGA, ° C. | C | H | N | S | Cl | C | H | N | S | Cl |
| 1 | 4-CH$_3$ | 35.8 | 211–12 | 189 | 50.61 | 3.25 | 10.42 | 15.89 | — | 50.54 | 3.34 | 10.47 | 15.42 | — |
| 2 | 4-Cl | 32.9 | 209–10 | 165 | 45.34 | 2.38 | 9.91 | 15.13 | 8.36 | 45.70 | 2.51 | 9.81 | 14.93 | 8.19 |
| 3 | 4-Cl | — | 211–12 | 185 | 45.34 | 2.38 | 9.91 | 15.13 | 8.36 | 45.44 | 2.39 | 9.48 | 14.68 | 8.26 |
| 4 | 4-NO$_2$ | 13.0 | 209–12 | 184 | 44.24 | 2.32 | 12.90 | 14.76 | — | 43.95 | 2.41 | 12.87 | 14.00 | — |

Preparation of Toners

A polyester binder (Atlac® 382ES, Reichhold Chemical) was heated and melted on a 4-inch two-roll melt-compounding mill. One of the rolls was heated and controlled to a temperature of 120° C., the other roll was cooled A Q/m measurement on 0.1 g developer from Vial # 1 was run using a charge-measuring apparatus described below. The conditions were: 0.1 g developer, 30 sec, 2000 V, negative polarity. The developer in Vial #1 was subsequently exercised on a bottlebrush device for 10 minutes. The bottlebrush consists of a cylindrical roll with a rotating magnetic core at 2000 revolutions per minute. The magnetic core has 12 magnetic poles arranged around its periphery in an alternating north-south fashion. This closely approximates the unreplenished aging of the developer in the electrostatographic development process. After this additional 10 minutes exercising the toner charge was measured on the charge-measuring apparatus. An "Admix-dust" measurement was run on this developer to estimate the amount of admix dust. Vial # 2 was subsequently placed on a bottlebrush device for 60 minutes. After this additional 60 minutes exercising the toner charge was measured on the charge-measuring apparatus.

Method of Charge Measurement

U.S. Pat. No. 5,405,727 describes the analytical test method for measuring the toner charge/mass ratio of this developer type. This method was employed to measure charge to mass of developers made with strontium ferrite carrier particles coated with polysiloxane. Toner charge/mass (Q/m) was measured in microcoulombs per gram of toner ($\mu$/gm) in the device. To measure the Q/m, a 100 mg sample of the charged developer was placed in the device and the charge to mass of the transferred toner was measured. This involves placing the 100 mg sample of the charged developer in a sample dish situated between a pair of circular parallel plates and subjecting it simultaneously for 30 seconds to a 60 Hz magnetic field and an electric field of about 200 volts/cm between the plates. The toner is thus separated from the carrier and is attracted to and collected on the top plate having polarity opposite to the toner charge. The total toner charge is measured by an electrometer connected to the plate, and that value is divided by the weight of the toner on the plate to yield the charge per mass of the toner (Q/m).

"Admix" Toner Dust Measurement

The propensity of developers to form low charging toner dust was measured using an "admix" dust test. This procedure has been described in U.S. Pat. No. 5,405,727. Admix dust values were determined by admixing 50% fresh toner (0.1 6 g) to the remaining developer and mixing lightly with to provide a final toner concentration of about 16%, followed by 30 second exercise on the wrist action shaker. This developer was then placed on a roll containing a rotating magnetic core, similar to a magnetic brush for electrostatic development. A weighing paper was placed inside the metal sleeve and the sleeve was placed over the brush and the end-piece was attached. The electrical connections were checked to ensure that the core was grounded. The electrometer was zeroed and the thow-off device was operated at 2000 rpm for 1 minute. The electrometer charge of the dust and the amount of dust collected on the weighing paper was measured and reported as the admix dust value (mg of dust), also referred to as TO (throw off).

Evaluation of Charging Properties

Effective charge control agents are ones that increase the absolute charge level of the toner relative to the control toner containing no charge control agent. The level of charge can generally be increased by increasing the concentration of the charge control agent.

Toners that charge rapidly and maintain that charge with extended exercise time are desirable. The initial Q/m indicates if the toner is charging rapidly. Measurements at 10 and 60 minutes indicate whether the material is maintaining a constant charge with life. This exercise time represents the mixing that the developer experiences in a electrophotographic printer.

Exercised toners that show a little or no decrease in Q/m over time are preferred over formulations that show a large decrease. A toner with a constant charge level will maintain a consistent print density when compared to a formulation that does not have a constant charge/mass level.

Clear toners with no pigment were used to determine if the CCA being evaluated had a triboelectric effect. Effective charge agents are the ones that increase the absolute charge level of the toner relative to the control toner containing no charge agent.

The triboelectric charge of electrophotographic developers changes with life. This instability in charging level is one of the factors that require active process control systems in electrophotographic printers to maintain consistent print to print in mage density. It is desirable to have charge/mass (Q/m) developers that are stable with life. The low Q/m has the advantage of improved electrostatic transfer and higher density capabilities.

It is desirable to lower the absolute Q/m of toners. The lower Q/m offers advantages of improved transfer and higher image densities. However, low Q/m is often achieved at a severe penalty in the throw-off (dust) amounts, which is undesirable as it results in a dusty developer. Low throw-off values (<10 mg of dust) combined with low Q/m (−10 to −40 $\mu$C/g) is desirable because we attain lower charge without paying the penalty of higher dust.

TABLE 2

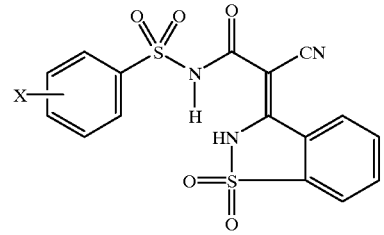

| EXAMPLE | Carrier Type* | Pigment | pph | Q/m, $\mu$C/g 2 min | Q/m $\mu$C/g 10 min | Q/m $\mu$C/g 60 min | Admix Dust, mg | X |
|---|---|---|---|---|---|---|---|---|
| C1 | A | Clear | 0 | −23.30 | −16.00 | −14.30 | — | 4-CH$_3$ |
| E2 | A | Clear | 1 | −43.20 | −42.20 | −42.70 | — | 4-CH$_3$ |
| E3 | A | Clear | 4 | −40.10 | −41.50 | −38.60 | — | 4-CH$_3$ |
| C4 | A | Clear | 0 | −23.30 | −16.00 | −14.30 | — | 4-Cl |
| E5 | A | Clear | 1 | −39.80 | −38.00 | −37.70 | — | 4-Cl |
| E6 | A | Clear | 4 | −43.60 | −33.30 | −30.20 | — | 4-Cl |
| C7 | B | Clear | 0 | −40.90 | −32.60 | — | — | 4-NO$_2$ |

TABLE 2-continued

| EXAMPLE | Carrier Type* | Pigment | pph | Q/m, μC/g 2 min | Q/m μC/g 10 min | Q/m μC/g 60 min | Admix Dust, mg | X |
|---|---|---|---|---|---|---|---|---|
| E8 | B | Clear | 2 | -44.10 | -18.20 | — | — | 4-NO$_2$ |
| C9 | B | Black | 0 | -47.00 | -39.00 | — | 25.5 | 4-CH$_3$ |
| E10 | B | Black | 1 | -41.80 | -32.40 | — | 9.2 | 4-CH$_3$ |
| E11 | B | Black | 4 | -32.40 | -17.20 | — | 11.7 | 4-CH$_3$ |
| C12 | B | Black | 0 | -44.70 | -37.60 | — | 35.2 | 4-Cl |
| E13 | B | Black | 1 | -37.20 | -27.40 | — | 15.6 | 4-Cl |
| C14 | B | Cyan (HB)** | 0 | -50.40 | -43.40 | — | 9.5 | 4-CH$_3$ |
| E15 | B | Cyan(HB) | 1 | -34.30 | -33.80 | — | 6.6 | 4-CH$_3$ |
| E16 | B | Cyan(HB) | 4 | -31.80 | -25.30 | — | 5.7 | 4-CH$_3$ |
| C17 | B | Cyan(HB) | 0 | -54.20 | -40.80 | — | 7.7 | 4-Cl |
| E18 | B | Cyan(HB) | 1 | -39.50 | -22.80 | — | 3.0 | 4-Cl |
| E19 | B | Cyan(HB) | 4 | -28.30 | -13.80 | — | 11.5 | 4-Cl |

*Carrier type A is silicone coated copper zinc ferrite; carrier type B is silicone coated strontium ferrite.
**HB is heliogen blue.

While specific embodiments of the invention have been shown and described herein for purposes of illustration, the protection afforded by any patent which may issue upon this application is not strictly limited to a disclosed embodiment but rather extends to modifications and arrangements which fall fairly within the scope of the claims which are appended hereto.

The invention has been described in detail with particular reference to certain preferred embodiments thereof, but it will be understood that variations and modifications can be effected within the spirit and scope of the invention.

What is claimed is:

1. An electrophotographic toner comprising a polymeric binder and an N-[2-(1,2-benzisothiazol-3(2H)-ylidene 1,1-dioxide)-2-cyanoacetyl]benzenesulfonamide as charge control agent having the structure:

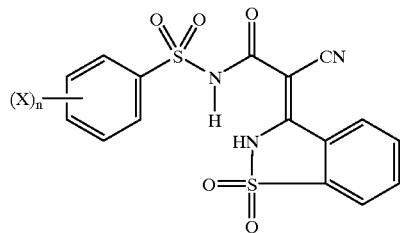

wherein
n represents an integer of 1 to 5 and
X represents hydrogen, alkyl, alkoxy, halo, nitro, amino, hydroxyl, carboalkoxy, carboxy, keto, formyl, alkyl sulfonate, sulfonamido or sulfamyl.

2. A toner composition according to claim 1 wherein X represents 4-chloro, 4-methyl or 4-nitro and n=1.

3. A toner composition according to claim 1 wherein the binder is a polyester having a glass transition temperature of 40 to 120° C. and a weight average molecular weight of 2,000 to 150,000.

4. A toner composition according to claim 1 wherein the binder is a polyester that is the non-linear reaction product of a dicarboxylic acid and a polyol blend of etherified diphenols.

5. An electrostatographic developer comprising a carrier and a toner composition according to claim 1.

6. An electrostatographic developer comprising a carrier and a toner composition according to claim 1, and further comprising a pigment.

7. A compound useful as a charge control agent, having the following structure:

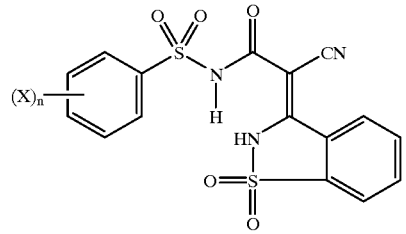

wherein
n represents an integer of 1 to 5 and
X represents hydrogen, alkyl, alkoxy, halo, nitro, amino, hydroxyl, carboalkoxy, carboxy, keto, formyl, alkyl sulfonate, sulfonamido or sulfamyl.

8. A compound according to claim 7 wherein X represents 4-chloro, 4-methyl or 4-nitro and n=1.

* * * * *